United States Patent [19]

Stein

[11] Patent Number: 5,466,855

[45] Date of Patent: Nov. 14, 1995

[54] FUNCTIONALIZED PEROXIDES FOR POLYMERIZATION REACTIONS

[75] Inventor: Daryl L. Stein, Bolingbrook, Ill.

[73] Assignee: Elf Atochem North America, Inc., Philadelphia, Pa.

[21] Appl. No.: 214,938

[22] Filed: Mar. 17, 1994

Related U.S. Application Data

[62] Division of Ser. No. 908,576, Jun. 25, 1992, Pat. No. 5,319,130, which is a continuation of Ser. No. 577,977, Sep. 5, 1990, abandoned.

[51] Int. Cl.⁶ .................................................. C07C 69/96
[52] U.S. Cl. .......................................... 558/263; 549/554
[58] Field of Search ............................................. 558/263

[56] References Cited

U.S. PATENT DOCUMENTS

| | | | |
|---|---|---|---|
| 3,660,468 | 5/1972 | McKellin | 525/327.3 |
| 3,725,455 | 4/1973 | D'Angelo et al. | 260/463 |
| 3,991,109 | 11/1976 | D'Angelo et al. | 260/544 Y |
| 4,180,518 | 12/1979 | Mageli et al. | 260/453 RZ |
| 4,483,781 | 11/1984 | Hartman | 562/2 |
| 4,525,308 | 6/1985 | Sanchez | 260/453 RZ |
| 4,526,726 | 7/1985 | Tang | 260/463 |
| 4,927,891 | 5/1990 | Kamath et al. | 260/488 |
| 4,956,416 | 9/1990 | Sanchez | 525/327.6 |
| 5,304,649 | 4/1994 | Sanchez et al. | 546/242 |

FOREIGN PATENT DOCUMENTS 0355733  2/1990  European Pat. Off. .

OTHER PUBLICATIONS

EPH No. 91114992.0 Search Report dated Dec. 5, 1991.
*The Kirk–Othmer Encyclopedia of Chemical Technology*, 3rd Ed., vol. 13, pp. 789–818 (1981).
*Polymer Handbook*, J. Brandrup & E. H. Immergut ed., John Wiley & Sons, Inc., pp. II–341 to II–362 (1966).

Primary Examiner—José G. Dees
Assistant Examiner—Barbara S. Frazier
Attorney, Agent, or Firm—Panitch Schwarze Jacobs & Nadel

[57] ABSTRACT

Novel functionalized peroxides which may be used as crosslinking, grafting and curing agents, initiators for polymerization reactions and as monomers for condensation polymerizations to form peroxy-containing polymers, which in turn can be used to prepare block and graft copolymers, have the following Formula I:

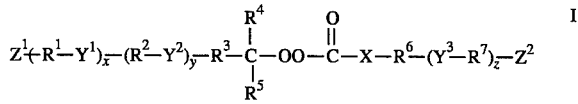

$R^1$, $R^2$, $R^3$, $R^4$, $R^5$, $R^6$, $R^7$, X, $Y^1$, $Y^2$, $Y^3$, $Z^1$, $Z^2$, x, y and z are as defined in the Summary of the Invention.

3 Claims, No Drawings

FUNCTIONALIZED PEROXIDES FOR POLYMERIZATION REACTIONS

This is a division of U.S. patent application Ser. No. 07/908,576, filed Jun. 25, 1992, now U.S. Pat. No. 5,319,130, which was a continuation of U.S. patent application Ser. No. 07/577,977, filed Sep. 5, 1990, now abandoned.

BACKGROUND OF THE INVENTION

1. Field of the Invention

This invention relates to novel functionalized peroxides. More particularly, this invention relates to novel functionalized peroxides which may be used as crosslinking, grafting and curing agents, initiators for polymerization reactions and as monomers for condensation polymerizations to form peroxy-containing polymers, which in turn can be used to prepare block and graft copolymers.

2. Description of the Prior Art

U.S. Pat. No. 3,660,468, assigned to the assignee of the present invention, discloses reacting alpha-carboxyisobutyryl chloride and related acid chlorides with hydroperoxides to form peresters containing a carboxy group. The compounds disclosed in this patent include monofunctional peroxides having a carboxy group and difunctional diperoxides having two carboxy groups. In contrast, the compounds of the present invention are multi-functionalized monoperoxides, having functional groups on both sides of the peroxide linkage. U.S. Pat. No. 3,660,468 also discloses difunctional monoperoxides having hydroxy and carboxyl groups. However, unlike the compounds of the present invention, the radical comprising the carbon atom alpha or adjacent to the perester carbonyl carbon in these prior art difunctional monoperoxides is a tertiary radical. That is, the alpha carbon has three other carbon atoms attached to it, not including the carbonyl carbon atom. In the compounds of the present invention, including peresters and other peroxy compounds, the radical comprising the carbon adjacent to the perester carbonyl carbon is only a primary or secondary radical. It is generally well known that peresters having a tertiary radical alpha to the carbonyl carbon are less thermally stable than peresters having a secondary radical alpha to the carbonyl carbon. These latter peresters are, in turn, less stable than peresters having a primary radical alpha to the carbonyl carbon. For example, in the series t-butyl peroxypivalate, t-butyl peroxyisobutyrate and t-butyl peroxypropionate, the ten hour half-life temperatures are 58° C., 82° C. and 101° C., respectively. In comparison, the peroxides of the present invention preferably have a ten hour half-life temperature greater than 60° C. and more preferably a ten hour half-life temperature of greater than 75° C.

SUMMARY OF THE INVENTION

The present invention relates to a compound having the following Formula I:

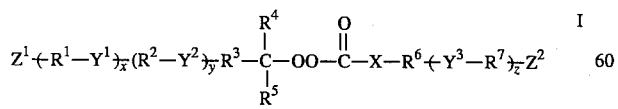

wherein $R^1$, $R^2$, $R^6$ and $R^7$ are independently a substituted or unsubstituted alkyl diradical of 1 to 18 carbons, a substituted or unsubstituted cycloalkyl diradical of 5 to 18 carbons, a substituted or unsubstituted bicycloalkyl diradical of 7 to 12 carbons, a substituted or unsubstituted bicycloalkenyl diradical of 7 to 12 carbons, a substituted or unsubstituted alkenyl diradical of 2 to 18 carbons, a substituted or unsubstituted alkynyl diradical of 2 to 18 carbons, a substituted or unsubstituted aralkyl diradical of 7 to 18 carbons, a substituted or unsubstituted naphthyl diradical or a substituted or unsubstituted diradical having the following Formula II:

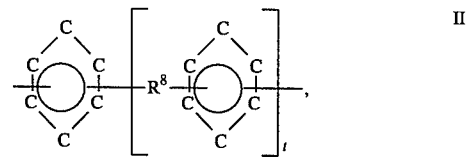

with the proviso that when X is a direct bond, $R^6$ is not a tertiary alkyl diradical;

$R^3$ is a substituted or unsubstituted alkyl diradical of 1 to 18 carbons, a substituted or unsubstituted aralkyl diradical of 7 to 18 carbons, a substituted or unsubstituted naphthyl diradical or the substituted or unsubstituted diradical having the Formula II;

$R^4$ and $R^5$ are independently a substituted or unsubstituted alkyl radical of 1 to 10 carbons;

$R^8$ is a direct bond, —O—, —S—, —S(=O)$_2$—, —C(=O)—, —C(=O)—O—, —O—C(=O)—, —O—C(=O)—O—, —NH—C(=O)—, —C(=O)—NH—, —NH—C(=O)—NH— or a substituted or unsubstituted alkyl diradical of 1 to 6 carbons;

X is a direct bond, —O— or —NH—;

$Y^1$, $Y^2$ and $Y^3$ are independently —O—, —S—, —S(=O)$_2$—, —C(=O)—, —C(=O)—O—, —O—C(=O)—, —O—C(=O)—O—, —NH—C(=O)—, —C(=O)—NH—, —NH—C(=O)—O—, —O—C(=O)—NH—, —NH—C(=O)—NH, —C(=O)—C(=O)—, —O—C(=O)—C(=O)—O—, —NH—C(=O)—C(=O)—NH—, —NH—C(=O)—C(=O)—O— or —O—C(=O)—C(=O)—NH—;

$Z^1$ and $Z^2$ are independently hydroxy, H$_2$N—, O=C=N—, Cl—C(=O)—, Br—C(=O)—, HO—C(=O)—,

HO—C($R^9$)($R^{10}$)—(CH$_2$)$_w$—Y$^1$—, H$_2$N—C($R^9$)($R^{10}$)—(CH$_2$)$_w$—Y$^1$— or $R^{11}$—O—C(=O)—;

$R^9$ and $R^{10}$ are independently hydrogen or a substituted or unsubstituted alkyl radical of 1 to 4 carbons;

$R^{11}$ is an alkyl radical of 1–4 carbons, benzyl or phenyl;

t, x, y and z are independently 0 or 1;

w is an integer from 1 to 12; and substituents for any of $R^1$, $R^2$, $R^3$, $R^4$, $R^5$, $R^6$, $R^7$, $R^8$, $R^9$ or $R^{10}$ are independently one or more of chloro, bromo, fluoro, cyano, hydroxy, amino, sulfo, carboxy, nitro, alkoxy of 1 to 12 carbons, alkylamino of 1 to 12 carbons, acyloxy of 1 to 12 carbons, alkenoyloxy of 3 to 12 carbons, alkenoylamino of 3 to 12 carbons, aroyloxy of 7 to 15 carbons, aroylamino of 7 to 15 carbons, phthalimido, alkoxycarbonyloxy of 2 to 13 carbons, alkoxycarbonylamino of 2 to 13 carbons, alkenyloxycarbonyloxy of 3 to 12 carbons, alkenyloxycarbonylamino of 3 to 12 carbons, aryloxycarbonyloxy of 7 to 15 carbons, alkylaminocarbonyloxy of 2 to 13 carbons, arylaminocarbonyloxy of 7 to 15 carbons, aralkylaminocarbonyloxy of 7 to 16 carbons, alkylsulfonyloxy of 1 to 8 carbons, alkylsulfonylamino of 1 to 8 carbons, arylsulfonylamino of 6 to 11 carbons or epoxyalkoxycarbonyl of 2 to 13 carbons.

The present invention also comprehends processes for preparing polycarbonate, polyester, polyamide, polyurea, polyimide, polyether and polyurethane polymers comprising reacting suitable monomers with a compound of Formula I.

The present invention also comprehends processes for polymerizing vinyl monomers with the perester compound of Formula I.

The present invention also comprehends processes for curing and crosslinking a polymer comprising reacting the polymer with a compound of Formula I.

The present invention also comprehends processes for preparing graft and block copolymers utilizing a compound of Formula I.

DETAILED DESCRIPTION OF THE PREFERRED EMBODIMENTS

The novel functionalized peroxides of the present invention have the following Formula I:

$$Z^1 + R^1 - Y^1\overline{)_x}(R^2 - Y^2\overline{)_y}R^3 - \underset{\underset{R^5}{|}}{\overset{\overset{R^4}{|}}{C}} - OO - \overset{\overset{O}{\|}}{C} - X - R^6 + Y^3 - R^7\overline{)_z}Z^2 \quad I$$

$R^1$, $R^2$, $R^3$, $R^4$, $R^5$, $R^6$, $R^7$, X, $Y^1$, $Y^2$, $Y^3$, $Z^1$, $Z^2$, x, y and z are as defined in the above Summary of the Invention.

Preferably, $R^1$, $R^2$, $R^6$ and $R^7$ are independently a substituted or unsubstituted alkyl diradical of 1 to 10 carbons, a substituted or unsubstituted cycloalkyl diradical of 5 to 12 carbons, a substituted or unsubstituted bicycloalkyl diradical of 7 to 10 carbons, a substituted or unsubstituted bicycloalkenyl diradical of 7 to 10 carbons, a substituted or unsubstituted alkenyl diradical of 2 to 8 carbons, a substituted or unsubstituted alkynyl diradical of 2 to 8 carbons, a substituted or unsubstituted aralkyl diradical of 7 to 12 carbons, a substituted or unsubstituted naphthyl diradical or a substituted or unsubstituted diradical of Formula II.

More preferably, $R^1$, $R^2$, $R^6$ and $R^7$ are independently a substituted or unsubstituted alkyl diradical of 1 to 6 carbons, a substituted or unsubstituted cycloalkyl diradical of 5 to 7 carbons, a substituted or unsubstituted bicycloalkyl diradical of 7 to 8 carbons, a substituted or unsubstituted bicycloalkenyl diradical of 7 to 8 carbons, a substituted or unsubstituted alkenyl diradical of 2 to 4 carbons, a substituted or unsubstituted aralkyl diradical of 7 to 12 carbons or a substituted or unsubstituted diradical of Formula II.

Preferably, $R^3$ is a substituted or unsubstituted alkyl diradical of 1 to 12 carbons, a substituted or unsubstituted aralkyl diradical of 7 to 12 carbons, a substituted or unsubstituted naphthyl diradical or a substituted or unsubstituted diradical of Formula II;

More preferably, $R^3$ is an alkyl diradical of 1 to 8 carbons.

Preferably, $R^4$ and $R^5$ are independently alkyl of 1 to 3 carbons.

Preferably, X is a direct bond or —O—.

Preferably, $Y^1$, $Y^2$ and $Y^3$ are independently —C(═O)—O— or —O—C(═O)—.

Preferably, $Z^1$ and $Z^2$ are independently hydroxy, —N═C═O, Cl—C(═O)—, HO—C(═O)—,

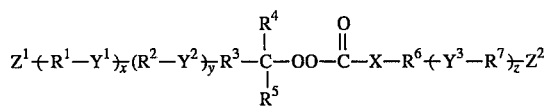

or $R^{11}$—O—C(═O)—.

More preferably, $Z^1$ and $Z^2$ are independently hydroxy, —N═C═O, Cl—C(═O)— or —HO—C(═O)—.

Preferable substituents for any of $R^1$, $R^2$, $R^3$, $R^6$ and $R^7$ are independently one or two of chloro, bromo, hydroxy, amino, carboxy, alkoxy of 1 to 6 carbons, acyloxy of 2 to 5 carbons, alkenoyloxy of 3 to 5 carbons or aroyloxy of 7 to 10 carbons.

More preferably substituents for any of $R^1$, $R^2$, $R^3$, $R^6$ and $R^7$ are independently chloro, hydroxy carboxy, alkoxy of 1 to 4 carbons, acyloxy of 2 to 3 carbons or alkenoyloxy of 3 to 5 carbons.

The compounds of Formula I may be prepared by reacting hydroxy-containing tertiary hydroperoxides with diacid halides, phosgene, dichloroformates, diisocyanates, anhydrides and lactones to form the functionalized peroxides. These reaction products may be further reacted, if desired, with dialcohols, diamines, aminoalcohols, epoxides, epoxy alcohols, epoxy amines, diacid halides, dichloroformates and diisocyanates to form additional functionalized peroxides.

The compounds of Formula I may be used as crosslinking, grafting and curing agents, initiators for polymerization reactions and as monomers for condensation polymerizations to form peroxy-containing polymers. These peroxy-containing polymers may then be used to prepare block and graft copolymers.

Generic Group Examples

As a substituted or unsubstituted alkyl diradical of 1–18 carbons, $R^1$, $R^2$, $R^3$, $R^6$ and $R^7$ may be, for example, 1,2-ethanediyl, 1,2-propanediyl, 1,3-propanediyl, 1,2-butanediyl, 2,3-butanediyl, 1,4-butanediyl, 1,6-hexanediyl, 1,5-pentanediyl, 1,12-dodecanediyl, 2,2-dimethyl-1,3-propanediyl, 1,8-octanediyl, 3-phenoxy-1,2-propanediyl, 3-isopropoxy-1,2-propanediyl, 3-methoxy-1,2-propane-1,2-diyl and 2-methoxy-1,3-propanediyl.

As a substituted or unsubstituted cycloalkyl diradical of 5–18 carbons, $R^1$, $R^2$, $R^6$ $R^7$ may be, for example, cyclohexane-1,2-diyl, cyclohexane-1,3-diyl, cyclohexane-1,4-diyl, 1,4-cyclohexanebis(methyl), 5-norbornene-2,3-diyl, isophoronediyl, 1,8-p-menthanediyl, 3,4,5,6-tetramethyl-1,2-cyclohexanediyl, 1-methyl-1,4-cyclohexanediyl, 1-methyl-1,3-cyclohexanediyl and the following diradical structures:

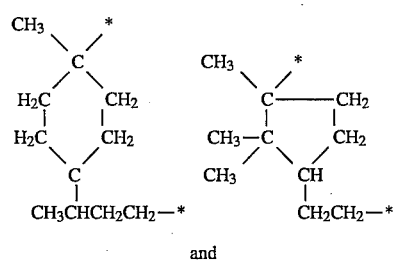

and

-continued

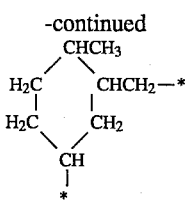

where * indicates the point of attachment of the diradical structures to the adjacent atoms in the compound of Formula I.

As a substituted or unsubstituted alkenyl diradical of 2–18 carbons, $R^1$, $R^2$, $R^6$ and $R^7$ may be, for example, ethylene-1,2-diyl, propene-2,3-diyl, 2-butene1,4-diyl, 3-octadecene-1,2-diyl, 3-dodecene-,1,2-diyl and 2,4-hexadiene-1,6-diyl.

As a substituted or unsubstituted alkynyl diradical of 2–18 carbons, $R^1$, $R^2$, $R^6$ and $R^7$ may be, for example, 2-butyn-1,4-diyl.

As a substituted or unsubstituted diradical of the following Formula II:

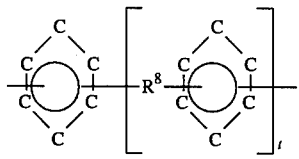

where t is 0 or 1 and $R^8$ is a direct bond or an alkyl diradical of 1–6 carbons, $R^1$, $R^2$, $R^3$, $R^6$ and $R^7$ may be, for example, benzene-1,2-diyl, benzene-1,3-diyl, benzene-1,4-diyl, 2-carboxybenzene-1,4-diyl, 4-carboxybenzene-1,2-diyl, 2-carbomethoxybenzene-1,4-diyl, 4-carboethoxybenzene-1,2-diyl, 4-nitrobenzene-1,2-diyl, 3,4,5,6-tetrabromobenzene-1,2-diyl, 3,4,5,6-tetrachlorobenzene-1,2-diyl, 2,2-propanebis(4-phenyl), biphenyl-4,4'-diyl, biphenyl-3,3'-diyl, biphenyl-3,4'diyl, methylenebis(4-phenyl)2-methylbenzene-1,5-diyl and 2-methylbenzene-1,3-diyl.

As a substituted or unsubstituted aralkyl diradical of 7–18 carbons, $R^1$, $R^2$, $R^3$, $R^6$ and $R^7$ may be, for example, methylbenzene-alpha,2-diyl, 1,4-benzenebis(methyl), 1,3-benzenebis(methyl) and 1,2-benzenebis(methyl As a substituted naphthyl diradical, $R^1$, $R^2$, $R^3$, $R^6$ and $R^7$ may be, for example, naphthalene-1,8-diyl, naphthalene-1,2-diyl, naphthalene-2,3-diyl, naphthalene-1,3-diyl, naphthalene-1,5-diyl, naphthalene-1,4-diyl, naphthalene-1,6-diyl, naphthalene-2,6-diyl, naphthalene-2,7-diyl, 4,5-dimenthoxy-naphthalene-1,8-diyl, 2-carboxynaphthalene-1,4-diyl, 2-carboxynaphthalene-3,5-diyl, 2,4-dinitronapholene-1,8-diyl, 4-bromonaphthalene-1,8-diyl, 4-chloro-naphthalene-1,8-diyl, 4,8-dicarboxynaphthalene-1,5-diyl, 5,8-dicarboxynaphthalene-1,4-diyl or 3-nitronaphthalene-1,8-diyl.

As an alkyl diradical of 1–6 carbons, $R^8$ may be, for example, methylene, 2,2-propanediyl, 1,1-ethanediyl and 1,2-ethanediyl.

As a substituted or unsubstituted alkyl radical of 1–10 carbons, $R^4$ and $R^5$ may be, for example, methyl, ethyl, propyl, butyl, octyl and decyl.

As a substituted or unsubstituted alkyl diradical of 1 to 6 carbons, $R^8$ may be, for example, methylene, bromomethylene, ethane-1,2-diyl, ethane-1,1-diyl, propane-1,2-diyl, propane-1,3-diyl, butane-1,2-diyl, butane-1,3-diyl, butane-1,4-diyl, propane-2,2-diyl, 1-carboxypropane-2,2-diyl, 1-(carboethoxy)propane-2,2-diyl, butane-1,4-diyl, pentane-2,2-diyl, butane-2,2-diyl, hexane-1,2-diyl, hexane-2,2-diyl, 4-cyanohexane-2,2-diyl, 1,1,1,3,3,3-hexafluoropropane-2,2-diyl, 2,2,2-trichloroethane-1,1-diyl, 1,3-dibromopentane-2,2-diyl and hexane-1,6-diyl.

As a substituted or unsubstituted alkyl radical of 1 to 4 carbons, $R^{10}$ and $R^{11}$ may be, for example, methyl, ethyl, propyl, isopropyl, butyl, isobutyl, sec-butyl, 2-ethoxyethyl, 2-methoxypropyl, 2-cyanoethyl, 2-bromoethyl, 3-chloropropyl, 2-acryloxyethyl, 2-methacryloxyethyl, 2-phthalimidoethyl, trifluoromethyl, 2,2,2-trifluoroethyl and 2-butoxyethyl.

List of Illustrative Compounds

Non-limiting examples of functionalized peroxides corresponding to compounds of Formula I of the present invention include:

1. 1,1-dimethyl-3-hydroxybutyl 6-(hydroxy)peroxyhexanoate
2. 1,1-dimethyl-3-{1-methyl-1-[4-(1-methyl-1-isocyanatoethyl)phenyl]ethylaminocarbonyloxy}butyl {1-methyl-1-[4-(1-methyl-1-isocyanatoethyl)phenyl]ethyl}peroxycarbamate
3. 1,1-dimethyl-3-[4-oxo-4-(2-hydroxyethylamino)butanoyloxy]butyl 4-oxo-4-(2-hydroxyethylamino) peroxybutanoate
4. OO-{1,1-dimethyl-3-[2-(hydroxyethoxy)carbonyloxy]butyl} O-[2-hydroxyethyl]monoperoxycarbonate
5. OO-{1,1-dimethyl-3-[(2-[chlorocarbonyloxy]ethoxy)carbonyloxy]butyl} O-[2-(chlorocarbonyloxy)ethyl] monoperoxycarbonate
6. OO-{1,1-dimethyl-3-[(glycidyloxycarbonyl)oxy]butyl} O-glycidyl monoperoxycarbonate
7. 1,1-dimethyl-3-(4-carboxybenzoyloxy)butyl 4-(carboxy)peroxybenzoate
8. 1,1-dimethyl-3-[3-(carboxy)undecanoyloxy]butyl 3-(carboxy)peroxyundecanoate
9. OO-[1,1-dimethyl-3-hydroxybutyl] O-[2-hydroxyethyl] monoperoxycarbonate
10. 1,1-dimethyl-3-[3-oxo-3-(4-aminophenylamino)propanoyloxy]propyl 3-oxo-3-(4-aminophenylamino)peroxypropionate
11. 1,1-dimethyl-3-[(3-carboxycyclohexyl)carbonyloxy]propyl (3-carboxycyclohexane)peroxycarboxylate
12. 1,1-dimethyl-3-{4'-[(2-hydroxypropyl)aminocarbonyl]biphen-4-ylcarbonyloxy}butyl 4'-[(2-hydroxypropyl)aminocarbonyl]biphen-4-ylperoxycarboxylate
13. 1,1-dimethyl-3-[(2-methyl-3-isocyanatophenyl)aminocarbonyloxy]propyl 6-[(2-methyl-3-isocyanatophenyl)aminocarbonyloxy]peroxyhexanoate
14. 1,1-dimethyl-3-[(2-methyl-3-isocyanatophenyl)aminocarbonyloxy]propyl 6-[(2-methyl-5-isocyanatophenyl)aminocarbonyloxy]peroxyhexanoate
15. 1,1-dimethyl-3-[(2-methyl-5-isocyanatophenyl)aminocarbonyloxy]propyl 6-[(2-methyl-3-isocyanatophenyl)aminocarbonyloxy]peroxyhexanoate
16. 1,1-dimethyl-3-[(2-methyl-5-isocyanatophenyl)aminocarbonyloxy]propyl 6-[(2-methyl-5-isocyanatophenyloxy ]peroxyhexanoate
17. 1,1-dimethyl-3-[(4-methyl-3-isocyanatophenyl)aminocarbonyloxy]propyl 6-[(4-methyl-3-isocyanatophenyl)aminocarbonyloxy]peroxyhexanoate Other examples of functionalized peroxides of this invention corresponding to compounds of Formula I would be readily apparent to one skilled in the art.

PREPARATION OF COMPOUNDS OF THE PRESENT INVENTION

The novel peroxides of this invention are prepared by reacting, optionally in the presence of a catalyst, hydroxy-hydroperoxides of Formula III:

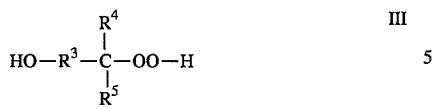

with about 1 to about 2 equivalents of a difunctional compound which is co-reactive with the hydroxy and/or hydroperoxy groups of the compounds of Formula III. Suitable co-reactive difunctional compounds to be used in the preparative methods of the present invention include compounds which are functional carbonate precursors, functional ester precursors, or urethane precursors. Optionally, additional reactions may be used to further modify the functional groups. These additional reactions are conducted depending on the subsequent use intended for the functional peroxide.

Non-limiting examples of suitable reactants to be used for preparing the novel peroxides of the present invention include:

(1) Suitable hydroxy-hydroperoxides of Formula III include 1,1-dimethyl-3-hydroxypropyl hydroperoxide, 1,1-dimethyl-3-hydroxybutyl hydroperoxide, 1-ethyl-3-hydroxy-1-methylpentyl hydroperoxide, 1,1-diethyl-3-hydroxybutyl hydroperoxide and 5-hydroxy-1,3,3-trimethylcyclohexyl hydroperoxide.

(2) Suitable carbonate and urethane precursors include phosgene, carbonyl bromide, Bisphenol-A bischloroformate, ethylene glycol bischloroformate, diethylene glycol bischloroformate, 1,4-butylene glycol bischloroformate, 1,6-hexylene glycol bischloroformate, 1,12-dodecanediol bischloroformate, 1,4-cyclohexanediol bischloroformate and 1,4-cyclohexanedimethanol bischloroformate.

(3) Suitable mono- and diester and mono- and diamide precursors include isophthaloyl chloride, terephthaloyl chloride, 4-(t-butyl)isophthaloyl chloride, 2,6-dichlorocarbonylnaphthalene, pyromellitic dianhydride, succinic anhydride, trimellitic anhydride, maleic anhydride, succinic anhydride, glutaric anhydride, phthalic anhydride, homophthalic anhydride, itaconic anhydride, 4-carboxyphthalic anhydride, citraconic anhydride, 4-amino-1,8-naphthalic anhydride, 4-chloro-1,8-naphthalic anhydride, 2-sulfobenzoic acid cyclic anhydride, tetrabromophthalic anhydride, tetrachlorophthalic anhydride, cis-5-norbornene-endo-2,3-dicarboxylic anhydride, 3,4,5,6-tetrahydrophthalic anhydride, 1,8-naphthalic anhydride, 4-nitrophthalic anhydride, trimellitic anhydride acid chloride, malonyl chloride 1,4-dichlorocarbonylcyclohexane, oxalyl chloride, succinyl chloride, adipoyl chloride, sebacoyl chloride, dodecanedioyl dichloride, suberoyl chloride, beta-butyrolactone, gamma-butyrolactone and epsilon-caprolactone.

(4) Suitable diurethane and diurea precursors include toluene-2,4-diisocyanate, toluene-2,6-diisocyanate and mixtures thereof (TDI), 1,5-naphthalene diisocyanate (NDI), 4,4'-methylenebis(phenylisocyanate) (MDI), 1,3- and 1,4-di-(1-isocyanato-1-methylethyl)benzenes, polymeric isocyanates as obtained by the phosgenation of polyamines produced from aniline and formaldehyde (known as PMDI), hexamethylene diisocyanate (HDI), trimethylhexamethylene diisocyanate (TMDI), isophorone diisocyanate (IPDI), methylenebis(cyclohexyl isocyanate), 1,4- and 1,3-bis(isocyanatomethyl)cyclohexanes, 1-isocyanato-1-methyl-4-isocyanatomethylcyclohexane, 1-isocyanato-1methyl-3-isocyanatomethylcyclohexane, 1-isocyanato-1-methyl-3-(2-isocyanatoethyl)cyclopentane, 1-isocyanato-2-isocyanatomethyl-4-isocyanatocyclohexane, 1-isocyanato-2-isocyanatomethyl-6-isocyanatocyclohexane, 1-isocyanato-4-isocyanatomethyl-2-isocyanatocyclohexane, 1-isocyanato-1,2,2-trimethyl-3-(2-isocyanatoethyl)cyclopentane p-xylylene diisocyanates. Other suitable di- and polyisocyanates are disclosed in *The Kirk-Othmer Encyclopedia of Chemical Technology*, 3rd Ed., Vol 13, pp. 89–818 (1981).

(5) Suitable optional di- or polyols include di- and polyhydric phenols, such as 1,3-dihydroxybenzene (resorcinol), 1,4-dihydroxybenzene (hydroquinone), 2-sulfo-1,4-hydroquinone, pentadecylresorcinol, Bisphenol-A (2,2-di(4-hydroxyphenyl)propane), 4,4'-dihydroxydiphenyl, di-(4-hydroxyphenyl)methane, 1,1-di-(4-hydroxyphenyl)cyclohexane, di-(4-hydroxyphenyl) sulfide, di-(4-hydroxyphenyl) sulfoxide, di-(4-hydroxyphenyl) sulfone, 2,2-di-(3,5-dichloro-4-hydroxyphenyl)propane, 2,2-di-(3,5-dibromo-4-hydroxyphenyl)propane, 2,2-di-(3,5-dimethyl-4-hydroxyphenyl)propane, 2,2-di(4-hydroxyphenyl)1,1,1,3,3,3-hexafluoropropane, phenolphthalein, di-(4-hydroxyphenyl) ketone and di-(4-hydroxyphenyl) ether, and aliphatic di- and polyhydroxy compounds, such as ethylene glycol, diethylene glycol, triethylene glycol, 1,2- and 1,3-propylene glycols, 1,2-, 1,3- and 1,4-butylene glycols, 1,6-hexanediol, 1,10-decamethylene glycol, 2,2-dimethyl-1,3-propanediol (neopentyl glycol), 2-buten-1,4-diol, 2-butyn-1,4-diol, 2,4,4-trimethyl-1,3-pentanediol, 1,4-cyclohexanediol, 1,4-cyclohexanedimethanol, glycerin, trimethylol propane and pentaerythritol.

(6) Suitable optional di- and polyamines include aromatic diamines, such as 1,3- and 1,4-phenylenediamines, 4,4'-diaminobiphenyl, di-(4-aminophenyl) ether, di-(4-aminophenyl) sulfide and di-(4-aminophenyl)methane and aliphatic diamines, such as ethylenediamine, hexamethylenediamine, 1,2-diaminopropane, 1,8-diaminooctane, 1,12-diaminododecane, 1,2-diamino-2-methylpropane, 1,2-diaminocyclohexane, 1,4-cyclohexanedimethylamine, 1,8-diamino-p-menthane and piperazine.

(7) Suitable optional di- and polyfunctional aminoalcohols include ethanolamine, propanolamine, diethanolamine, 4-amino-1-butanol, 4-aminocyclohexanol, 2-aminohexanol, 2-amino-2-methylpropanol, 6-aminohexanol, dipropanolamine, 2,2-dimethyl-3-aminopropanol, p-aminophenol and m-aminophenol.

(8) Suitable optional epoxides include ethylene oxide, propylene oxide, butylene oxide, epichlorohydrin, styrene oxide, glycidol, glycidol methyl ether, glycidol propyl ether and glycidol phenyl ether.

(9) Suitable optional catalysts are bases including one or more of triethylamine, tributylamine, N,N-dimethylaniline, pyridine, 4-(N,N-dimethylamino)pyridine, 1-azabicyclo(2.2.2)octane, 1,4-diazabicyclo(2.2.2)octane, 1,8-diazabicyclo(5.3.0)undec-7-ene, sodium hydroxide, sodium carbonate, sodium hydrogen carbonate, potassium hydroxide, potassium carbonate, potassium hydrogen carbonate, calcium hydroxide, barium hydroxide, calcium carbonate and trisodium phosphate, for example. In the cases where the co-reactive difunctional compounds are diurethane precursors, for example, diisocyanates, the optional catalysts can also be one or more of a Lewis acid, such as methylsulfonic acid and p-methylphenylsulfonic acid, a metal compound, such as di-n-butyltin diacetate, di-n-butyltin dioctoate, di-n-butyltin dilaurate and phenyllead triacetate.

Several synthesis methods are available for preparing the novel functional peroxides of this invention.

The reactions are optionally conducted in the presence of a catalyst and water or other suitable solvent. Examples of suitable catalysts are as set forth above. Examples of suitable solvents include aromatic, aliphatic and chlorinated hydrocarbons, such as benzene, chlorobenzene, toluene, hexane and methylene chloride, ethers, such as tetrahydrofuran (THF) and diethylether, and low molecular weight esters such as ethyl acetate. Other suitable solvents to be used in accordance with the present invention would be readily apparent to one skilled in the art. The specific synthesis techniques may be determined readily by a chemist of ordinary skill in the art by reference to standard works in the chemical literature, if necessary, in addition to the following general methods and specific working examples. Variations in techniques due to specific reactants, etc., may be readily determined based on the present disclosure without undue experimentation.

Novel functional peresters of this invention may be prepared by reacting the hydroxy-hydroperoxides of Formula III and suitable ester precursors. The reaction is conducted at suitable temperatures, to yield a desired perester. In accordance with the present invention, suitable temperatures at which the compounds of Formula III may be reacted with suitable ester precursors are about $-5°$ C. to about $60°$ C.

Novel functional peresters of this invention of exemplary Formulas IA and/or IB derived from Formula I may be prepared by reacting the hydroxy-hydroperoxides of Formula III with suitable ester precursors as illustrated by the following non-limiting exemplary equation:

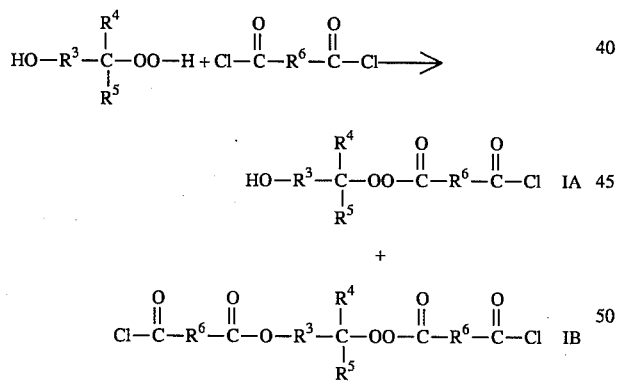

IA is a compound derived from Formula I where $Z^1$ is HO—, $Z^2$ is —C(=O)—Cl, X is a direct bond, x, y and z are zero, and $R^3$, $R^4$, $R^5$ and $R^6$ are as previously broadly defined.

IB is a compound derived from Formula I where $Z^1$ is Cl—C(=O)—, $Z^2$ is —C(=O)—Cl, $Y^2$ (created by the reaction) is —C(=O)—O—, X is a direct bond, x and z are zero, y is 1, $R^3$, $R^4$ and $R^5$ are as previously broadly defined and $R^6$ and $R^2$ are the same and as previously broadly defined.

In the above reaction affording products IA and/or IB, it is readily apparent to one of ordinary skill in the art that the primary reaction product may be a compound of Formula IA or a compound of Formula IB, or the reaction product may be a mixture of compounds of Formulas IA and IB, depending on the amounts of starting reagents used, the reactivity of the starting reagents, reaction times and reaction temperatures.

Optional subsequent reactions of compounds of Formulas IA and IB with other suitable reagents as described hereinbefore provide additional latitude for choice of other functional groups. An example of one further reaction with the compound of Formula IA follows:

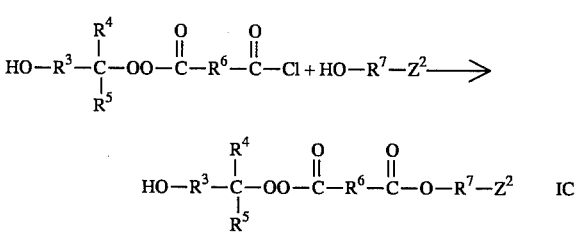

IC is a compound derived from Formula I where $Z^1$ is HO—, $Y^3$ (created by the reaction) is —C(=O)—O—, X is a direct bond, x and y are zero, z is 1, and $R^3$, $R^4$, $R^5$, $R^6$, $R^7$ and $Z^2$ are as previously broadly defined.

Similarly, reacting HO—$R^7$—$Z^2$ with the compound of Formula IB will give the corresponding reaction with one or both of the —C(=O)—Cl groups of $Z^1$ and $Z^2$. Furthermore, if a mixture of alcohols corresponding to the formula HO—$R^7$—$Z^2$, where the $R^7$ groups are different, is reacted with a mixture of the compounds of Formula IA and IB, the resulting product will be a product mixture of all possible permutations. One of ordinary skill in the art would readily recognize the possible permutations of reaction products.

Novel peroxycarbamates of this invention may be prepared by reacting the hydroxy-hydroperoxides of Formula III and suitable diurethane precursors (e.g., diisocyanates) as illustrated by the following non-limiting exemplary equation:

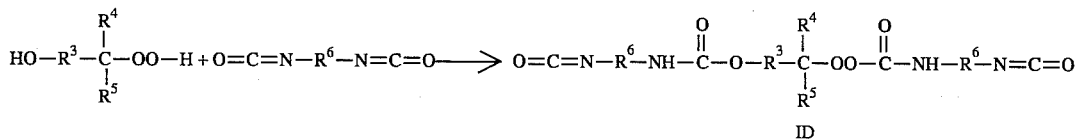

where $Z^1$ and $Z^2$ are each $-N=C=O$, $Y^2$ is $-NH-C(=O)-O-$, $X$ is $-NH-$, $x$ and $z$ are zero, $y$ is 1, $R^3$, $R^4$ and $R^5$ are as previously broadly defined and $R^6$ and $R^2$ are the same and as previously broadly defined. Mixtures of diisocyanates can be used. A subsequent reaction, for example with an alcohol, can provide additional latitude for choice of other functional groups, as illustrated by the following non-limiting exemplary equation:

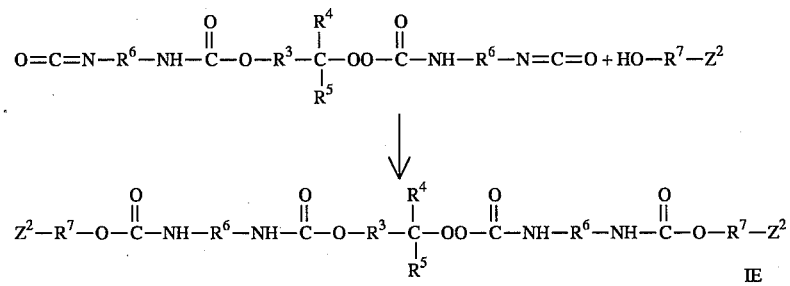

where $Z^1$ and $Z^2$ are the same, $Y^1$ (created by the reaction) is $-O-C(=O)-NH-$, $Y^3$ (created by the reaction) and $Y^2$ are $-NH-C(=O)-O-$, $X$ is $-NH-$, $x$, $y$ and $z$ are 1, $R^3$, $R^4$ and $R^5$ are as previously broadly defined, $R^6$ and $R^2$ are the same and as previously broadly defined and $R^7$ and $R^1$ are the same and as previously broadly defined. If desired, mixtures of various alcohols could be used, resulting in mixtures of various corresponding peroxycarbamates.

Novel monoperoxycarbonates of this invention having exemplary Formulas IF and/or IG may be prepared by reacting the hydroxy-hydroperoxides of Formula III and suitable carbonate precursors as illustrated by the following non-limiting exemplary equation:

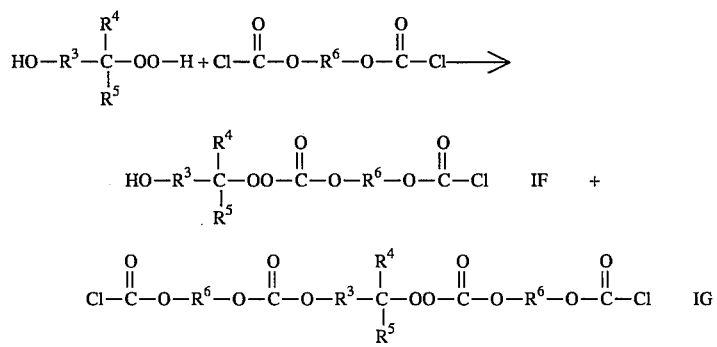

IF is a compound derived from Formula I where $Z^1$ is $HO-$, $Z^2$ is $-O-C(=O)-Cl-$, $X$ is $-O-$, $x$, $y$ and $z$ are zero, and $R^3$, $R^4$, $R^5$ and $R^6$ are as previously broadly defined.

IG is a compound derived from Formula I where $Z^1$ is $Cl-C(=O)-O-$, $Z^2$ is $-O-C(=O)-Cl$, $Y^2$ (created by the reaction) is $-O-C(=O)-O-$, $X$ is $-O-$, $x$ and $z$ are zero, $y$ is 1, $R^6$ and $R^2$ are the same and are as previously broadly defined, and $R^3$, $R^4$ and $R^5$ are as previously broadly defined.

In the above reaction affording products IF and/or IG, it is readily apparent to one of ordinary skill in the art that the primary reaction product may be a compound of Formula IF or a compound of Formula IG, or the reaction product may be a mixture of compounds of Formulas IF and IG, depending on the amounts of starting reagents used, the reactivity of the starting reagents, reaction times and reaction temperatures.

Optional subsequent reactions can provide additional latitude for choice of other functional groups. An example using the compound of Formula IG follows:

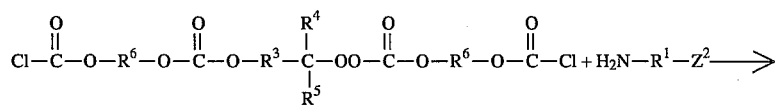

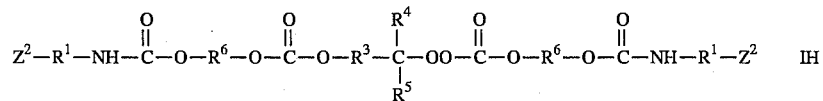

where $Z^1$ and $Z^2$ are the same and are as previously broadly defined, $Y^1$ and $Y^3$ (both created by the reaction) are —NH—C(=O)—O— and —O—C(=O)—NH—, respectively, $Y^2$ is —O—C(=O)—O—, X is —O—, x, y and z are 1, $R^1$ is the same as $R^7$ as previously broadly defined, $R^3$, $R^4$ and $R^5$ are as previously broadly defined and $R^6$ and $R^2$ are the same and are as previously broadly defined.

Another route to both the novel peresters and the novel monoperoxycarbonates of this invention is by ester interchange (transesterification). In this route, a diester of a dicarboxylic acid (e.g., dimethyl isophthalate, dimethyl terephthalate, etc.) is the diester precursor for the perester, and a dialkyl carbonate (e.g., dimethyl carbonate, diethyl carbonate, diphenyl carbonate, etc.) is the carbonate precursor for the monoperoxycarbonate. The other raw materials are the same except that an ester interchange catalyst is employed instead of a catalyst/base. Non-limiting examples of suitable ester interchange catalysts include alkali metal alkoxides, such as sodium methoxide, and tetraalkyl titanates, such as tetrapropyl titanate. An exemplary transesterification equation follows, resulting in compounds of Formula IJ, IK or mixtures thereof:

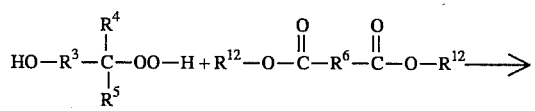

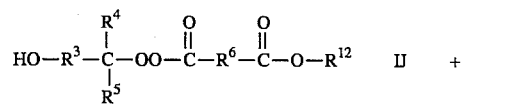

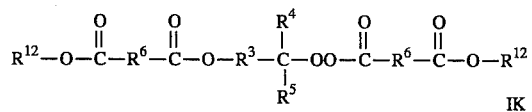

IJ is a derivative of the compound of Formula I where $Z^1$ is HO—, $Z^2$ is —C(=O)—O—$R^{12}$, X is a direct bond, x, y and z are zero, $R^3$, $R^4$, $R^5$ and $R^{12}$ are as previously broadly defined, and $R^6$ and $R^2$ are the same and as previously broadly defined.

IK is a derivative of the compound of Formula I where $Z^1$ is $R^{12}$—O—C(=O)—, $Z^2$ is —C(=O)—O—$R^{12}$, $Y^2$ (created by the reaction) is —C(=O)—O—, X is a direct bond, x and z are zero, y is 1, $R^3$, $R^4$, $R^5$ and $R^{12}$ are as previously broadly defined, and $R^6$ and $R^2$ are the same as previously broadly defined.

In the above reaction affording products IJ and/or IK, it is readily apparent to one of ordinary skill in the art that the primary reaction product may be a compound of Formula IJ or a compound of Formula IK, or the reaction product may be a mixture of compounds of Formulas IJ and IK, depending on the amounts of starting reagents used, the reactivity of the starting reagents, reaction times and reaction temperatures.

As in the other above examples, the reactants used to prepare the peroxides of the present invention may be mixtures.

As a further example, the following sequence demonstrates another process to prepare a functional peroxide using a mixture of reactants:

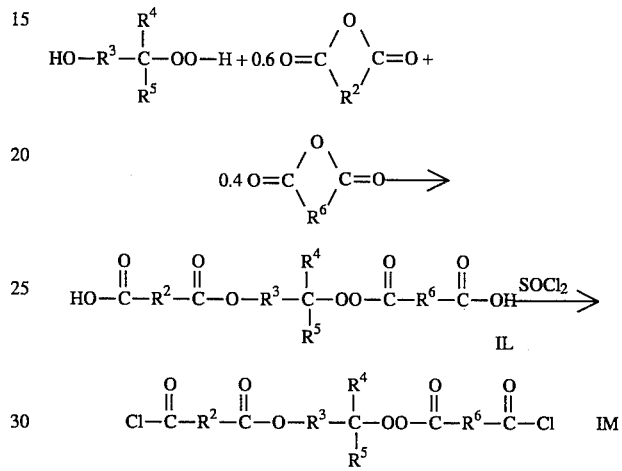

IL is a derivative of the compound of Formula I where $Z^1$ is HO—C(=O)—, $Z^2$ is —C(=O)—OH, $Y^2$ (created by the reaction) is —C(=O)—O—, X is a direct bond, x and z are zero, y is 1, and $R^2$, $R^3$, $R^4$, $R^5$ and $R^6$ are as previously broadly defined, but $R^2$ and $R^6$ are not necessarily the same.

IM is a derivative of the compound of Formula I where $Z^1$ is Cl—C(=O)—, $Z^2$ is —C(=O)—Cl—, $Y^2$ is —C(=O)—O—, X is a direct bond, x and z are zero, y is 1, and $R^2$, $R^3$, $R^4$, $R^5$ and $R^6$ are as previously broadly defined, but $R^2$ and $R^6$ are not necessarily the same.

Further reaction of IM with a mixture of alcohols, for example, produces a product having a mixture of components, as well as a mixture of different products. One such exemplary product is produced as illustrated in the following non-limiting exemplary equation:

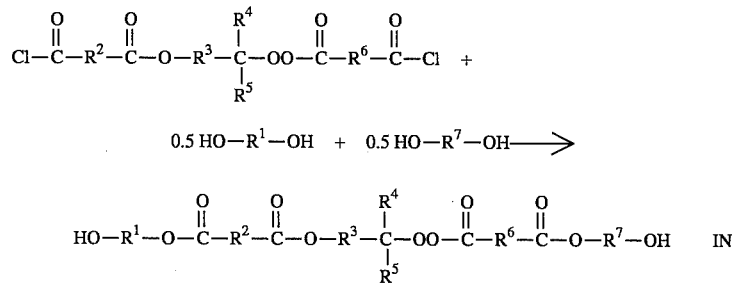

IN is a derivative of the compound of Formula I where $Z^1$ is HO—, $Z^2$ is —OH, $Y^1$ (created by the reaction) is —O—C(=O)—, $Y^3$ (created by the reaction) and $Y^2$ are —C(=O)—O—, X is a direct bond, x, y and z are 1, and $R^1$, $R^2$, $R^3$, $R^4$, $R^5$, $R^6$ and $R^7$ are as previously broadly defined, but $R^1$ and $R^7$ are not necessarily the same and $R^2$ and $R^6$ are not necessarily the same.

Utility

The novel peroxides of the present invention are suitable monomers or comonomers for use in condensation polymerizations, such as condensation polymerization reactions for synthesizing polycarbonates, polyesters, polyamides, polyureas, polyethers, and polyurethanes. When the functionalized peroxides of this invention are used as comonomers in combination with other condensation monomers (CMs), a peroxide linkage becomes incorporated into the backbone of the polymer, as illustrated by the following equation:

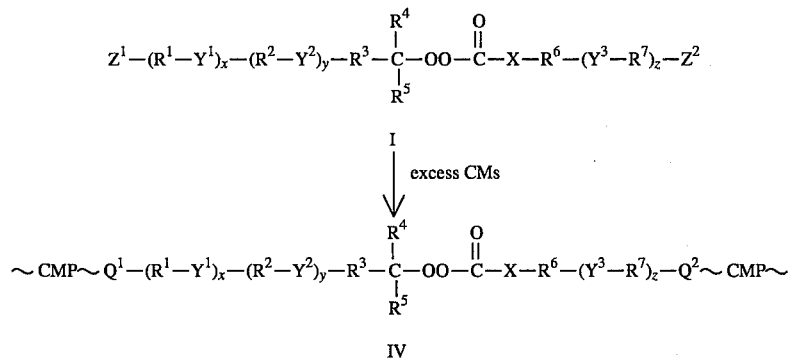

$R^1$, $R^2$, $R^3$, $R^4$, $R^5$, $R^6$, $R^7$, X, $Y^1$, $Y^2$, $Y^3$, $Z^1$, $Z^2$, x, y and z are as previously defined. $Q^1$ and $Q^2$ are groups formed in the polymerization reaction as a result of $Z^1$ and $Z^2$ reacting with one or more condensation monomers (CMs), and CMP is the condensation monomer polymer.

The compounds of Formula IV so prepared can be used for producing compatibilizing block copolymers containing condensation monomer polymer blocks (CMP) and addition monomer polymer blocks (AMP) via free-radical initiation of polymerization of addition monomers (AMs) with the polymeric-peroxides formed. This block polymerization reaction is illustrated by the following equation:

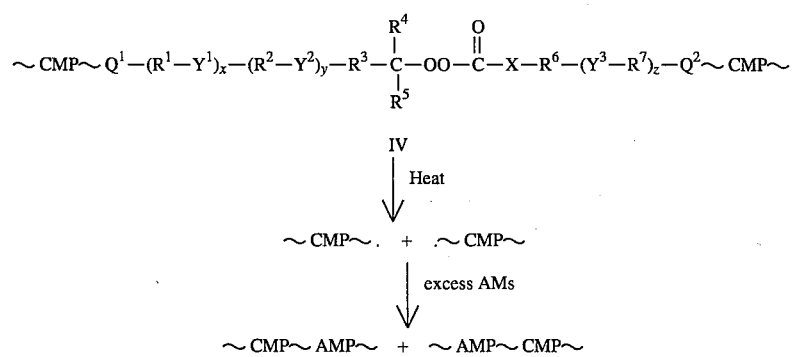

where CMP and AMP represent the condensation monomer polymer blocks and addition monomer polymer blocks, respectively.

Polymeric-peroxides derived from the peroxy-monomers of this invention are more useful than the polymeric-peroxides of the prior art. They are useful for preparing block copolymers that contain lower amounts of homopolymers, because the peroxide unit is in the backbone of polymers, and decomposition of the peroxide unit generates two macro-free-radicals. The macro-free-radicals initiate the polymerization of ethylenically unsaturated monomers which results only in formation of two block copolymer units (AB block copolymers). Thus, no homopolymer forms.

In accordance with the present invention, the polymeric-peroxides can also be used for the following:

(1) to compatibilize polymers in situ in reactive processing by forming block copolymers in polymer processing equipment, such as extruders, roll mills, etc.;

(2) for quality enhancement of interpenetrating polymer networks (IPN's) in polymer processing equipment;

(3) to enhance the impact resistance of polymer blends in reactive processing;

(4) as polymeric low profile/low shrink curing agents, as self-curing polymeric systems and as self-degrading polymer systems;

(5) as highly desirable polymeric-peroxide masterbatches which are safe, easily dispersible polymeric-peroxide compositions having up to 5% or more of organic peroxides, useful in crosslinking, curing and polymer modification applications, the peroxide functions being compatible and covalently bonded with the polymer backbone so that they cannot bloom, exude or volatilize; and (6) in initiating polymerization of ethylenically unsaturated monomers, in curing of unsaturated polyester resin compositions, for crosslinking/curing of elastomers, for crosslinking of olefin polymers, for graft polymerizing monomers onto other polymer backbones and for controlling the melt rheology of olefin polymers, such as polypropylene (PP) and polyethylene (PE).

The novel peroxides of this invention are suitable initiators for use in vinyl polymerizations, for example, for synthesizing polyolefins, polyacrylics, polystyrene, poly(vinyl chloride), etc. Other unsaturated polymers to be prepared using the novel peroxides of this invention would be readily apparent to one skilled in the art. When the functionalized peroxides of this invention are used as initiators, the functional groups become attached as end groups on the polymer formed:

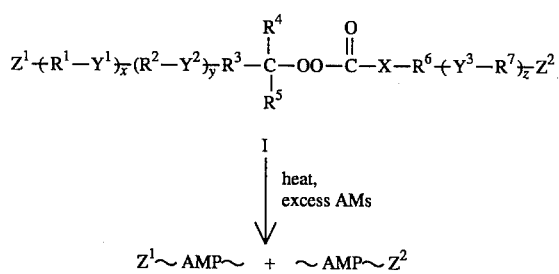

$R^1$, $R^2$, $R^3$, $R^4$, $R^5$, $R^6$, $R^7$, X, $Y^1$, $Y^2$, $Y^3$, $Z^1$, $Z^2$, x y and z are as previously broadly defined. The functional groups $Z^1$ and $Z^2$ can be used as chemical "handles" to attach performance additives, such as antioxidants, UV stabilizers, and fire retardants onto the polymer, thus extending the useful life of the polymers. The polar nature of the functional group can make the polymer more amenable to other added components to a polymer formulation, such as fillers, pigments, stabilizers and the like. The functional group could also be used as a site for the initiation of condensation polymerizations to yield block copolymers with properties as discussed above.

The functional initiators of the present invention are useful for the polymerization or copolymerization of ethylenically unsaturated monomers or mixtures thereof at suitable temperatures. The compounds are useful not only in conventional isothermal polymerization processes, but also in processes in which two or more increasing temperature steps are used or a continuous increase in temperature is used. Suitable ethylenically unsaturated monomers to be polymerized using the compounds of the present invention include olefins, such as ethylene, propylene, styrene, alpha-methylstyrene, chlorostyrene, vinyl benzyl chloride, vinyl toluene, vinyl pyridine, divinyl benzene; diolefins, such as 1,3-butadiene, isoprene and chloroprene; vinyl esters, such as vinyl acetate, vinyl propionate, vinyl laurate, vinyl benzoate or divinyl carbonate; unsaturated nitriles, such as acrylonitrile and methacrylonitrile; acrylic acid, methacrylic acid and their esters and amides, such as methyl, ethyl, n-butyl, 2-ethylhexyl and 2-hydroxyethyl acrylates and methacrylates and acrylamide and methacrylamide; maleic anhydride; maleimide and N-substituted derivatives thereof, such as N-phenylmaleimide; maleic and fumaric acids and their esters; vinyl halo and vinylidene halo compounds, such as vinyl chloride, vinyl bromide, vinyl fluoride, vinylidene chloride and vinylidene fluoride; perhalo olefins, such as tetrafluoroethylene, hexafluoropropylene and chlorotrifluoroethylene; vinyl ethers, such as methyl vinyl ether, ethyl vinyl ether, n-butyl vinyl ether; allyl alcohol; allyl esters, such as allyl acetate, allyl benzoate, diallyl phthalate, allyl ethyl carbonate, triallyl phosphate, triallyl cyanurate, diallyl fumarate, diallyl succinate, and diallyl carbonate; acrolein; methyl vinyl ketone; and mixtures thereof.

Examples of other suitable vinyl monomers and comonomers that can be used in this invention are given in *Polymer Handbook*, J. Brandrup and E. H. Immergut ed., John Wiley & Sons, Inc., pp. II-341 to II-362 (1966), and are hereby incorporated herein by reference.

In accordance with the present invention, temperatures of about 30° C. to about 250° C. and preferably, about 40° C. to about 200° C., may be used in the conventional polymerization or in the increasing temperature polymerization processes. In addition, peroxide levels of about 0.005 to about 5% and preferably about 0.01 to about 1%, by weight, based on monomer, may be used in the conventional polymerization or in the increasing temperature polymerization processes. Polymerization may be carried out in solution, where suitable solvents, such as toluene, may be used. Bulk, solution, suspension or emulsion polymerization processes may be used. The functional peroxides of the present invention may also be used in these vinyl polymerization processes alone or together with other peroxide and azo initiators, as is generally known to those skilled in the art.

The functional peroxide initiators of this invention are also useful for producing high impact polymers, such as high impact polystyrene, by initiating grafting a monomer onto the backbone of elastomers or rubbers, such as polybutadienes, styrene-butadiene-styrene triblock copolymers, ethylene-propylene-diene terpolymers, etc. These initiators may also be used with lower amounts of the rubber to produce high impact resistant polymers having impact resistance comparable to high impact polymers produced with larger amounts of rubber and conventional initiator systems. The above described vinyl polymerization conditions and initiator levels up to 15% by weight of rubber, based on monomer, may be used for producing high impact polymers.

The polymers of the present invention may also be used to prepare acrylic coatings. Acrylic pre-polymers or pre-copolymers (generically "pre-polymers"), suitable for coatings application, in both lacquer and enamel compositions, typically comprise polymerized monomers of alkyl acrylate and/or alkyl methacrylate, hydroxyalkyl acrylate and/or hydroxyalkyl methacrylate, acrylic acid and/or methacrylic acid, and the like. Acrylic enamel coating resins generally need contain chemically active groups, such as hydroxy or carboxy groups, to undergo molecular weight buildup and network formation during the final curing or crosslinking reaction. Curing compounds, such as melamine formaldehyde or isocyanates may be used as the curing agents.

To prepare a pre-polymer with the desired functionality suitable for use in enamel formulation, a suitable amount of hydroxyalkyl acrylate and/or hydroxyalkyl methacrylate is used. This assures that each polymer chain formed has a crosslinking site or hydroxy group incorporated therein. The peroxides of the present invention can assure this result by attaching at least one such functional group to the end of each polymer chain formed by initiation. Thus, at least some if not all of the expensive hydroxyalkyl acrylate and/or methacrylate can be replaced by using a functional peroxide, while providing better control over the functional groups content and location. Such acrylic compositions are further discussed in U.S. Pat. No. 4,927,891, assigned to the assignee of the present invention, and incorporated herein by reference.

Unsaturated polyester resins that can be cured by the initiators of this invention usually include an unsaturated polyester and any polymerizable monomers. The unsaturated polyesters are, for example, obtained by esterifying at least one ethylenically unsaturated di- or polycarboxylic acid, anhydride, or acid halide, such as maleic acid, fumaric acid, glutaconic acid, itaconic acid, mesaconic acid, citraconic acid, allylmalonic acid, allylsuccinic acid and tetrahydrophthalic acid, among others, with saturated or unsaturated di- or polyols, such as ethylene glycol, diethylene glycol, triethylene glycol, 1,2- and 1,3-propanediols, 1,2-, 1,3- and 1,4-butanediols, 2,2-dimethyl-1,3-propanediol, 2-(hydroxymethyl)-2-methyl1,3-propanediol, 2-buten-1,4-diol, 2-butyn-1,4-diol, 2,2,4-trimethyl-1,3-pentanediol, glycerol, pentaerythritol and mannitol, among others. Other suitable ethylenically unsaturated di- or polycarboxylic acid, anhydride or acid halide and other saturated or unsaturated di- or polyol to be used in accordance with the present invention would be readily apparent to one skilled in the art. Mixtures of such polyacids and mixtures of such polyalcohols may also be used.

The unsaturated di- or polycarboxylic acids may be partly replaced by saturated polycarboxylic acids, such as adipic acid, succinic acid and sebacic acid, among others, or by aromatic, polycarboxylic acids, such as phthalic acid, trimellitic acid, pyromellitic acid, isophthalic acid and terephthalic acid. The acids used may be substituted, for example, by halogen groups. Non-limiting examples of suitable halogenated acids include, for example, tetrachlorophthalic acid and 5,6-dicarboxy-1,2,3,4,7,7-hexachlorobicyclo[2.2.1]heptene, among others.

The components of the unsaturated polyester resin, including the polymerizable monomer or monomers, are preferably ethylenically unsaturated monomers, such as styrene, chlorostyrene, vinyl toluene, divinyl benzene, alpha-methylstyrene, diallyl maleate, diallyl phthalate, dibutyl fumarate, acrylonitrile, triallyl phosphate, triallyl cyanurate, methyl acrylate, methyl methacrylate, n-butyl methacrylate and ethyl acrylate, among others, and mixtures thereof, which are copolymerizable with the polyesters.

A preferred unsaturated polyester resin contains as the polyester component the esterification product of a polyalcohol, such as 1,2-propylene glycol, an anhydride of an unsaturated polycarboxcylic acid, such as maleic anhydride and an anhydride of an aromatic dicarboxylic acid, such as phthalic anhydride, and the monomer component styrene.

Other unsaturated polyester resins that are useful in the processes of the present invention include unsaturated vinyl ester resins having a vinyl ester component and any polymerizable monomer components. The vinyl ester resin component may be made by reacting a chloroepoxide, such as epichlorohydrin, with suitable amounts of a glycol, such as bisphenol-A (2,2-(4-hydroxyphenyl)propane), in the presence of a base, such as sodium hydroxide, to yield a condensation product having terminal epoxy groups derived from epichlorohydrin. Subsequent reaction of the condensation product with polymerizable unsaturated carboxylic acids in the presence or absence of acidic or basic catalysts, results in the formation of a vinyl ester terminated resin component. Generally, styrene is added as the polymerizable monomer component to complete the preparation of the unsaturated vinyl ester resin.

In accordance with the present invention, temperatures of about 20° C. to about 200° C. and peroxide levels of about 0.05 to about 5% or more by weight of curable unsaturated polyester resin are normally used in the curing process. The unsaturated polyester resins described above can be filled with various materials, such as sulfur, glass fibers, carbon blacks, silicas, metal silicates, clays, metal carbonates, antioxidants, heat and light stabilizers, sensitizers, dyes, pigments, accelerators, metal oxides, such as zinc oxide, blowing agents, etc. Other suitable or desirable materials to be added to the unsaturated polyester resins would be readily apparent to one skilled in the art.

The following examples are presented to provide a more detailed explanation of the present invention and are intended as illustrations and not limitations of the invention.

EXAMPLE 1

The Reaction of 1,1-Dimethyl-3-hydroxybutyl Hydroperoxide with Glutaric Anhydride In this Example, the preparation of a compound of the following structure is described:

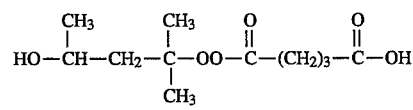

An Erlenmeyer flask was charged with 16.6 grams (g) (141 mmole) of 97% glutaric anhydride, 21.4 g (212 mmole) of triethylamine, 0.86 g (7 mmole) of 4-N,N'-dimethylaminopyridine and 40 g of methylene chloride to form a clear, light-yellow solution. The solution was cooled to 0° C. using an ice-salt bath, causing some of the anhydride to precipitate. An ice cold solution of 21.6 g (141 mmole) of 87.8% 1,1-dimethyl-3-hydroxybutyl hydroperoxide in 10 g of methylene chloride was added. About half of the solution was added in one portion, causing the temperature of the solution to rise to 20° C. The other half was added over a period of about 5 minutes, during which the temperature was maintained at about 15° C. The reaction mixture was stirred at 0°–5° C. for 2 hours (h), whereupon additional glutaric anhydride (2 g, for a total of 18.6 mmole) was added. The reaction mixture was maintained an additional hour at 0°–5° C. and was then maintained at room temperature for 1 hour. The reaction mixture was then washed 3 times with a 33% monosodium phosphate solution, and the organic layer was dried over magnesium sulfate and suction filtered. After removal of the solvent using a rotary evaporator, 34.6 g (98.8%) of a viscous yellow oil was obtained. Analysis of the oil indicated 6.1% residual hydroperoxide. The corrected Active[O] (for hydroperoxide) was 3.95%. The theoretical Active[O] was 6.44%. Accordingly, the oil assayed at 61.4% for desired product.

EXAMPLE 2

The Reaction of Two Equivalents of Glutaric Anhydride with 1,1-Dimethyl-3-hydroxybutyl Hydroperoxide In this Example, the preparation of a compound of the following structure is described:

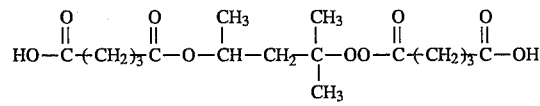

An Erlenmeyer flask was charged with 22.7 g (193 mmole) of 97% glutaric anhydride, 19.5 g (193 mmole) of triethylamine, 0.86 g (7 mmole) of 4-N,N'-dimethylaminopyridine and 40 g of methylene chloride to form a clear, light-yellow oil. The solution was cooled to 10° C. and a cold solution of 14.8 g (96.6 mmole) of 87.8% 1,1-dimethyl-3-hydroxybutyl hydroperoxide in 10 g of methylene chloride was added at such a rate that the reaction temperature stayed below 25° C. The solution was stirred at 25° C. for another 1.5 h before it was washed with three 100 g portions of 33% monosodium phosphate solution. The organic layer was then dried over magnesium sulfate and suction filtered. Removal of the solvent yielded 33.2 g (94.7%) of a dark red oil. Analysis by high performance liquid chromatography indicated that the oil contained less than 0.5% of the starting hydroperoxide. The Active[O] was 3.97%. The theoretical Active[O] was 4.42%. Accordingly, the oil assayed at 88.7% for desired product.

EXAMPLE 3

Reaction of Maleic Anhydride with 1,1-Dimethyl-3-hydroxybutyl Hydroperoxide

In this Example, the preparation of a compound of the following structure is described:

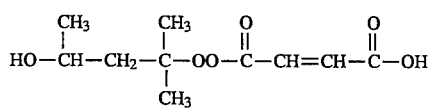

An Erlenmeyer flask was charged with 6.57 g (43.1 mmole) of 87.8% 1,1-dimethyl-3-hydroxybutyl hydroperoxide, 6.54 g (64.6 mmole) of triethylamine, 0.23 g (1.9 mmole) of 4-N,N'-dimethylaminopyridine and 15 g of methylene chloride. The resulting solution was cooled in an ice-salt bath to 0° C., and 6.34 g (64.6 mmole) of powdered maleic anhydride was added in small portions over 10 min. After the reacton mixture was stirred for 45 min, it was washed with three 20 g portions of 33% monosodium phosphate solution and once with water. The solution was dried over magnesium sulfate and was suction filtered. Removal of the solvent yielded 7.7 g (77%) of a dark viscous oil. Analysis by high performance liquid chromatography indicated that the oil contained 1.5% residual hydroperoxide. The corrected Active[O] was 3.77%. The theoretical Active[O] was 6.89%. Accordingly, the oil assayed at 54.7% for desired product.

EXAMPLE 4

Reaction of 1,1-Dimethyl-3-hydroxybutyl Hydroperoxide with Two Equivalents of Adipoyl Chloride Followed by Reaction with Ethylene Glycol In this Example, the preparation of a compound of the following structure is described:

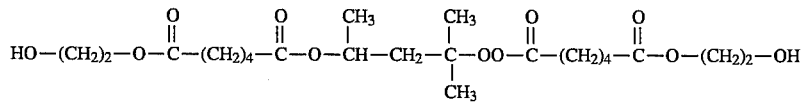

A 3-necked 250 mL flask equipped with a thermometer and addition funnel was charged with 23 g (123 mmole) of 98% adipoyl chloride and about 50 g of dry ethyl acetate to form a clear solution. To this magnetically stirred solution was added dropwise over 15–30 min, a mixture of 10 g (61.1 mmole) of 82% 1,1-dimethyl-3-hydroxybutyl hydroperoxide (anhydrous), 20 g (253 mmole) of pyridine, 0.1 g (0.8 mmole) of 4-N,N'-dimethylaminopyridine and 50 g of ethyl acetate The temperature of the reaction mixture was held between 20°–25° C. After an additional 15 minutes of stirring, 15 g (242 mmole) of ethylene glycol was quickly added. After 0.5 h of stirring, the reaction mixture was washed with water, once with 10% HCl soln, twice with water and once with 2% sodium bicarbonate solution. The organic phase was dried over magnesium sulfate and suction filtered. Removal of the solvent yielded 8.2 g (27.2%) of a light yellow oil. Analysis by high performance liquid chromatography indicated 1.2% residual hydroperoxide and less than 0.5% residual ethylene glycol.

EXAMPLE 5

Reaction of 1,1-Dimethyl-3-hydroxybutyl Hydroperoxide with Two Equivalents of Succinic Anhydride In this Example, the preparation of a compound of the following structure is described:

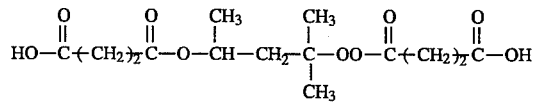

A jacketed reactor equiped with an agitator, thermometer, and an addition funnel was charged with 1,600 g of dry ethyl acetate, 202.0 g (2.0 mole) of 99% succinic anhydride, 1.2 g (0.01 mole) of 4-N,N-dimethylaminopyridine and 161.0 g (2.04 mole) of pyridine. The ingredients were stirred at 30°–32° C. to form a clear solution which was cooled to 10° C. 147.0 g (1.0 mole) of 91% 1,1-dimethyl-3-hydroxybutyl hydroperoxide was then added over 10 minutes. 154.7 g (1.5 moles) of triethylamine was then added over 30 minutes while the temperature was held at about 10° C. The resultant slurry was stirred for 2 h at 30° C. and for another 2 h at 40° C. The reaction mass was cooled to 0° C., diluted with 200 g of water and neutralized to pH 3 with 900 g of 40% phosphoric acid. The organic layer was separated and washed with 500 g of 10% monosodium phosphate solution. The organic phase was dried over 100 g of sodium sulfate and suction filtered. The organic phase was then dried over 100 g of magnesium sulfate and was refiltered. To the filtered viscous oil was added 2,800 g of pentane, causing the product to separate out as a bottom layer. The pentane/ethyl acetate upper layer was decanted off. Residual solvent was removed from the product by stripping it under vacuum to yield 209.0 g of a viscous oil. The analysis of the oil was as follows: Active[O] found 4.21%, expected 4.79%; assay 88.0%, crude yield 62.5%, corrected yield 55.0%, residual water 2.7%, residual ethyl acetate 1.7%, residual succinic acid <0.1% and residual pyridine <0.1%.

EXAMPLE 6

Preparation of a Peroxy Containing Polymer Using a Compound of This Invention

Part A. Reaction of the product of Example 5 with phosgene to form a diacid chloride.

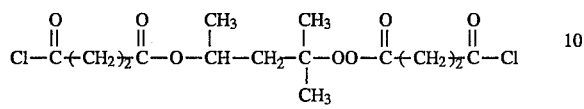

A 4-necked jacketed reactor was fitted with a mechanical stirrer, a thermometer, a nitrogen inlet line, and a graduated addition funnel fitted with a dry ice filled Dewar condenser. The reactor was charged with 200 g of methyl t-butyl ether, 1.0 g (0.013 mole) of pyridine, and 38.9 g (0.124 mole) of the product of Example 5. The resultant solution was cooled to 0° C. and 20.2 g (0.2 mole) of phosgene was added dropwise from the addition funnel over 20 minutes. A moderate exotherm was observed. The reaction mass temperature was raised to 20°–22° C. for 2 h. The reaction mixture was then sparged with nitrogen and the solvent was removed under reduced pressure to yield 42.0 g (91.6%) of a waxy solid.

Part B. Reaction of the acid chloride of Part A with a dihydroxy terminated oligomer to form a peroxy containing polymer.

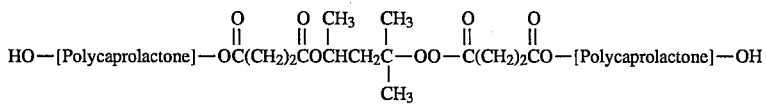

A 4-necked jacketed reactor was fitted with a mechanical stirrer, a thermometer and an addition funnel. The reactor was charged with 100 g of tetrahydrofuran, 5.9 g (0.075 mole) pyridine, 0.13 g (0.001 mole) of 4-N,N-dimethylaminopyridine and 31.5 g (0.015 mole) of TONE® 240 (a dihydroxy terminated polycaprolactone oligomer produced by the Union Carbide Corp., M.W. 2,000). 8.0 g (0.013 mole) of the product of Part B were then added at 20°–22° C. over 1.5 h. The reaction mixture temperature was raised to 50°–52° C. for 2 h before 0.08 g of n-butanol was added. After another 20 minutes at 50° C., the reaction mixture was cooled to 0° C. and was washed with 100 g of 3% HCl. The phases were separated and the organic phase was washed with 3% sodium bicarbonate and then with 100 g of methanol. Removal of the solvent under reduced pressure yielded 24.0 g (70.7%) of a waxy solid. Analysis of this material by gel permeation chromatography gave Mn of 6,000 Mw of 8,000 and Mz of 10,000 which indicated polymer had formed. The polymer had an Active[O] of 0.04%, indicating a peroxide was incorporated.

EXAMPLE 7

Preparation of a mixture of 1,1-dimethyl-3-hydroxybutyl 2-(carboxy)perbenzoate and 1,1-dimethyl-3-(2-carboxybenzoyloxy)butyl 2-(carboxy)perbenzoate

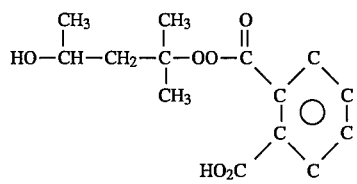

and

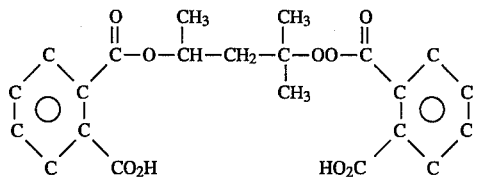

A reactor was set up equipped with a mixer, a thermometer, an addition funnel and an external cooling and heating apparatus. Methyl t-butyl ether (100 g), phthalic anhydride (23.1 g, 0.155 mole), 4-(dimethylamino)pyridine (0.24 g) and pyridine (15.4 g, 0.2 mole) were mixed together at 30°–32° C. to dissolve the phthalic anhydride, followed by cooling to 10° C. 1,1-Dimethyl-3-hydroxybutyl hydroperoxide (24.2 g of 86.1% material, 0.115 mole) was added at 8°–10° C. over 10 minutes. The slurry was mixed at 30° C. for 5 h and was then cooled to 0° C. Water (100 g) and 40% aqueous phosphoric acid (10 g) were added to neutralize the slurry to a pH of 3. The organic phase was washed with 20% aqueous sodium dihydrogen phosphate solution (20 g), and dried over anhydrous magnesium sulfate (15 g). Pentane (100 g) was then added to force a bottom separation of product. The upper solvent layer was decanted. The product was slurried with an additional 100 g pentane and the upper layer was decanted again. The residual viscous liquid was concentrated using aspirator and high vacuum systems to give 22.0 g of product. Wet chemical analysis of the product showed an active oxygen content of 3.41%, less than 0.2% residual hydroperoxide and less than 0.2% residual hexylene glycol. Liquid chromatography (LC) indicated the presence of both 1:1 and 2:1 products in a ratio of 7:1 (theoretical active oxygen content 5.43%). LC and active oxygen analyses combined to give a 60% assay 1,1-dimethyl-3-hydroxybutyl 2-(carboxy)perbenzoate and 2.6% 1,1-dimethyl-3-(2-carboxybenzoyloxy)butyl 2-(carboxy)perbenzoate. The infrared spectrum for this mixture showed the expected broad OH of the alcohol and carboxylic acid(s) 2800–3300 $cm^{-1}$ and a broad signal for the mixed ester, perester and acid carbonyls at 1700–1770 $cm^{-1}$.

EXAMPLE 8

Preparation of a mixture of
1,1-dimethyl-3-hydroxybutyl
2-(carboxy)peroxycycyclohexanecarboxylate and
1,1-dimethyl-3-(2-carboxycyclohexane-
carbonyloxy)butyl-2-(carboxy)peroxycyclohexane-
carboxylate

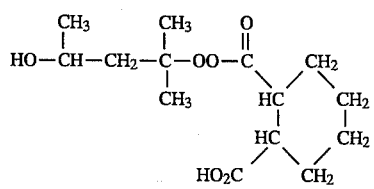

and

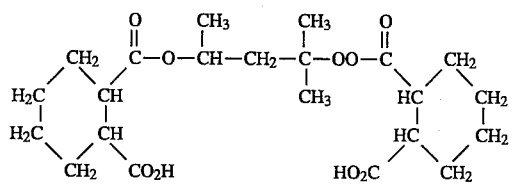

Ethyl acetate (50 g), hexahydrophthalic anhydride (Milldride Chemical Co., 16.0 g, 0.1 mole), sodium acetate (3.3 g, 0.04 mole) and 4-dimethylaminopyridine (0.6 g, 0.005 mole) were combined in an open, covered reactor equipped with a mixer, a thermometer, an addition funnel and an external cooling and heating apparatus. The resulting mixture was mixed for 10 minutes at 30° C., followed by cooling to 0° C. Dry 1,1-dimethyl-3-hydroxybutyl hydroperoxide (assay 86.1%, 16.0 g, 0.1 mole) was added at 10°–12° C. over 10 minutes. The slurry was warmed to 35° C. and mixed at 35°–40° C. for three hours. The slurry was then cooled to −10° C., filtered to remove solids and the volatile components were stripped off under vacuum to yield 30.0 g of a waxy solid. Wet chemical analyses showed an active oxygen content of 4.68% with 4.6% unreacted hydroperoxide, <0.2% residual hexylene glycol and 4.2% unreacted 1,2-cyclohexanedicarboxylic anhydride. Liquid chromatographic analysis (LC) indicated the presence of both the 1:1 adduct and 2:1 adduct in a ratio of 3:1. LC and active oxygen analyses were combined to estimate an assay of 68.7% of the 1:1 adduct, 1,1-dimethyl-3-hydroxybutyl 2-(carboxy)peroxycyclohexanecarboxylate and 23.9% of the 2:1 adduct, 1,1-dimethyl-3-(2-carboxycyclohexanecarbonyloxy)butyl 2(carboxy)peroxycyclohexanecarboxylate. The recovery was 88% based on starting hydroperoxide. The infrared spectrum for the mixture showed the expected broad OH band of the alcohol and carboxylic acid(s) at 2800–3300 cm$^{-1}$ and a broad signal for the mixed ester, perester and acid carbonyls at 1650–1780 cm$^{-1}$. The DSC analysis of this mixture showed an exotherm peak for the decomposition of the perester at 135° C.

EXAMPLE 9

Preparation of a mixture of
1,1-dimethyl-3-hydroxybutyl 2-carboxy-4(or
5)-(methyl) peroxycyclohexanecarboxylate and
1,1-dimethyl-3-(2-carboxy-4(or
5)-methylcyclohexyl carbonyloxy)butyl
2-Carboxy-4-(or 5)
(methyl)peroxycyclohexanecarboxylate

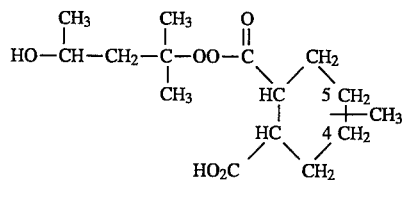

and

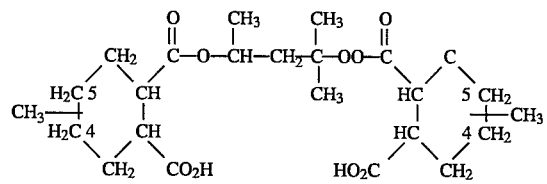

The procedure of Example 8 was used with dry 1,1-dimethyl-3-hydroxybutyl hydroperoxide (assay 86.1%, 60.0 g, 0.1 mole), 4-methylhexahydrophthalic anhydride (Milldride Chemical Co., 17.0 g, 0.1 mole), sodium acetate (3.3 g, 0.04 mole), 4-dimethylaminopyridine (0.6 g, 0,005 mole) and ethyl acetate (60.0 g) to form 29.0 g of the title mixture. Wet chemical analyses showed an active oxygen content of 4.04% with 7.3% unreacted 1,1-dimethyl-3-hydroxybutyl hydroperoxide, <0.2% residual hexylene glycol and 3.5% unreacted 4-methyl-1,2-cyclohexanedicarboxylic anhydride. Liquid chromatographic analysis (LC) indicated the presence of both the 1:1 adduct and 2:1 adduct in a ratio of 5:2. LC and active oxygen analyses were combined to estimate an assay of 56.4% of the 1:1 adduct, 1,1-dimethyl-3-hydroxybutyl 2-carboxy-4(or 5)-(methyl)peroxycyclohexanecarboxylate and 31.0% of the 2:1 adduct, 1,1-dimethyl-3-(2-carboxy-4(or 5)-methylcyclohexylcarbonyloxy)butyl 2-carboxy-4(or 5)-(methyl)peroxycyclohexanecarboxylate. The recovery was 73% based on starting hydroperoxide. The infrared spectrum for the mixture showed the expected broad OH band of the alcohol and carboxylic acid(s) at 2800–3300 cm$^{-1}$ and a broad signal for the mixed ester, perester and acid carbonyls at 1650–1780 cm$^{-1}$. The DSC analysis of this mixture showed a peak exotherm for the decomposition of the perester group at 135° C.

EXAMPLE 10

Preparation of a mixture of
1,1-dimethyl-3-hydroxypropyl
3-(carboxy)peroxypropanoate and
1,1-dimethyl-3-(3-carboxypropanoyloxy)propyl
3-(carboxy)peroxypropanoate

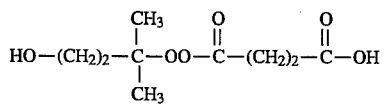

-continued and

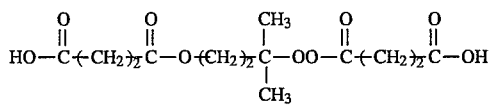

Ethyl acetate (40 g) and succinic anhydride (22.2 g, 0.2 mole) were combined in an open, covered reactor equipped with a mixer, a thermometer, an addition funnel and an external cooling and heating apparatus. This mixture was stirred and heated to 50°–55° C. for 10 minutes to dissolve the anhydride. The mixture was cooled to 20° C. and sodium acetate (1.6 g, 0.02 mole) and 4-dimethylaminopyridine (0.12 g) were added and mixing continued for 5 minutes. 1,1-Dimethyl-3-hydroxypropyl hydroperoxide (assay 88%, 13.6 g, 0.1 mole) was added over 10 minutes at 20°–22° C. The slurry was warmed to 40° C. and stirred for 1 hour. The slurry was then cooled to −20° C. and filtered to remove solids. The solvent was removed under aspirator vacuum to give 36.0 g of a waxy solid. Wet chemical analyses showed an active oxygen content of 3.42%, and 0.9% water. Liquid chromatographic analysis (LC) indicated the presence of both the 1:1 and 2:1 adducts in a ratio of 1:3.6. LC and active oxygen analyses combined to estimate the product compositions as 48.6% 1,1-dimethyl-3-hydroxypropyl 3-(carboxy)peroxypropanoate and 3.5% 1,1-dimethyl-3-(3-carboxypropanoyloxy)propyl 3-(carboxy)peroxypropanoate. The recovery was 77% based on starting hydroperoxide. The DSC analysis of this mixture showed an exotherm peak for the decomposition of the perester at 162° C. The infrared spectrum of the product mixture showed the broad OH absorbance at 3000–3500 cm$^{-1}$ and the broad carbonyl absorbance for the perester and carboxy groups at about 1700–1740 cm$^{-1}$.

EXAMPLE 11

Preparation of a mixture of 1,1-dimethyl-3-hydroxybutyl 3-(carboxy)-5-norbornene-2-ylperoxycarboxylate and 1-dimethyl-3-(3-carboxy-5-norbornene-2-ylcarbonyloxy)butyl 3-(carboxy)-5-norbornene-2-ylperoxycarboxylate

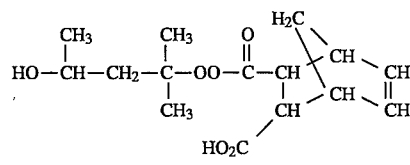

and

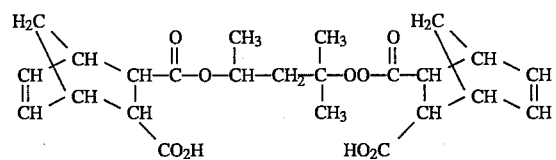

Tetrahydrofuran (30 g) and norbornene-2,3-dicarboxylic anhydride (36.4 g, 0.22 mole) were combined in an open, covered reactor equipped with a mixer, a thermometer, an addition funnel and an external cooling and heating apparatus. This mixture was stirred and heated to 50°–52° C. for 10 minutes to dissolve the anhydride. The mixture was cooled to 30° C. and ethyl acetate (30 g), sodium acetate (8.4 g, 0.1 mole) and 4-dimethylaminopyridine (0.6 g) were added. 1,1-Dimethyl-3-hydroxypropyl hydroperoxide (assay 86.1%, 31.2 g, 0.2 mole) was added over 10 minutes at 30° C. The mixture was stirred for 4 hours at 30°–35° C. The mixture was then cooled to −20°C. and filtered to remove solids. The solvent was removed under aspirator vacuum to give 79.0 g of a waxy solid. Wet chemical analyses showed an active oxygen content of 2.48%, 2.5% water, 3% residual starting hydroperoxide and 15.2% norbornene dicarboxylic anhydride. Liquid chromatographic analysis (LC) indicated the presence of both the 1:1 and 2:1 adducts in a ratio of 3.8:1. LC and active oxygen analyses combined to estimate the product composition as 33.9% 1,1-dimethyl-3-hydroxybutyl 3-(carboxy)-5-norbornene-2-ylperoxycarboxylate and 8.8% 1,1-dimethyl-3-(3-carboxy-5-norbornene-2-ylcarbonyloxy)butyl 3-(carboxy)-5-norbornene-2-ylperoxycarboxylate. The recovery was 52.5% based on starting hydroperoxide. The DSC analysis of this mixture showed an exotherm peak for the decomposition of the perester at 139° C. The infrared spectrum of the product mixture showed the broad OH absorbance at 3100–3300 cm$^{-1}$ for the hyudroxyl and carboxy groups and the broad carbonyl absorbance for the perester and carboxy groups at about 1722 cm$^{-1}$.

EXAMPLE 12

1,1-Dimethyl-3-hydroxybutyl Hydroperoxide/Trimellitic Anhydride

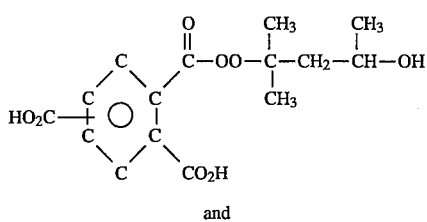

and

-continued

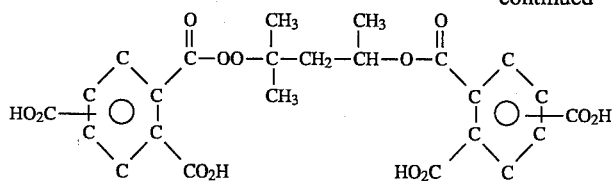

Tetrahydrofuran (40 g) and trimellitic anhydirde (TMA, 43.6 g, 0.22 mole) were combined in an open, covered reactor equipped with a mixer, a thermometer, an addition funnel and an external cooling and heating apparatus. The mixture was stirred at 60° C. for 10 minutes to dissolve the anhydride and then cooled to 30° C. Ethyl acetate (40 g), sodium acetate (8.4 g, 0.1 mole) and 4-dimethylaminopyridine (0.6 g, 0.005 mole) were added and the resulting mixture was stirred for 10 minutes then cooled to 25° C. Dry 1,1-dimethyl-3-hydroxybutyl hydroperoxide (assay 86.1%, 31.2 g, 0.2 mole) was added at 25°–30° C. over 10 minutes. The resulting heavy slurry was mixed for 2 hours at 45°–50° C. The mixture was filtered hot and the filtrate was then cooled to −20° C. and refiltered, thereby removing any inorganic salts. Volatile components were stripped off under aspirator vacuum to give 66.0 g of a waxy solid. Wet chemical analysis indicated the active oxygen content was 3.10%. There was little residual starting hydroperoxide, but 12.7% residual trimellitic anhydride. Liquid chromatographic (LC) analysis indicated the presence of both 1:1 and 2:1 adducts in a ratio of 49:1. LC and active oxygen analyses combined to estimate the product composition as 58.1% 1:1 adduct and 1.2% 2:1 adduct. The recovery was 60% based on starting hydroperoxide. DSC analysis showed a decomposition exotherm for the perester at 131° C. The infrared spectrum of the product mixture showed the broad OH absorbance of 3000–3300 cm$^{-1}$ for the hydroxyl and carboxyl groups and the broad carbonyl absorbance for the perester and carboxyl groups at about 1710 cm$^{-1}$.

The present invention may be embodied in other specific forms without departing from the spirit or essential attributes thereof and, accordingly, reference should be made to the appended claims, rather than to the foregoing specification as indicating the scope of the invention.

I claim:

1. A compound having the following Formula I:

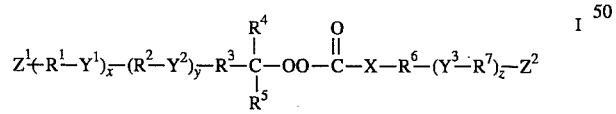

wherein

R$^1$, R$^2$, R$^6$ and R$^7$ are independently a substituted or unsubstituted alkyl diradical of 1 to 18 carbons, a substituted or unsubstituted cycloalkyl diradical of 5 to 18 carbons, a substituted or unsubstituted bicycloalkyl diradical of 7 to 12 carbons, a substituted or unsubstituted bicycloalkenyl diradical of 7 to 12 carbons, a substituted or unsubstituted alkenyl diradical of 2 to 18 carbons, a substituted or unsubstituted alkynyl diradical of 2 to 18 carbons, a substituted or unsubstituted aralykl diradical of 7 to 18 carbons, a substituted or unsubstituted naphthyl diradical or a substituted or unsubstituted diradical having the following Formula II:

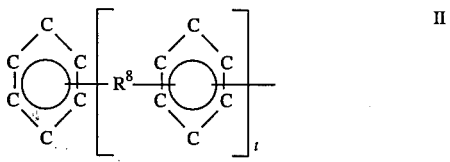

R$^3$ is a substituted or unsubstituted alkyl diradical of 1 to 18 carbons, a substituted or unsubstituted aralkyl diradical of 7 to 18 carbons, a substituted or unsubstituted naphthyl diradical or the substituted or unsubstituted diradical having the Formula II;

R$^4$ and R$^5$ are independently a substituted or unsubstituted alkyl radical of 1 to 10 carbons;

R$^8$ is a direct bond, —O—, —S—, —S(=O)$_2$—, —C(=O)—, —C(=O)—O—, —O—C(=O)—, —O—C(=O)—, —NH—C(=O)—, —C(=O)—NH—, —NH—C(=O)—NH— or a substituted or unsubstituted alkyl diradical of 1 to 6 carbons;

X is —O—;

Y$^1$, Y$^2$ and Y$^3$ are independently —O—S—, —S(=O)$_2$—, —C(=O)—, —C(=O)—O—, —O—C(=O)—, —O—C(=O)—O—, —NH—C(=O)—, —C(=O)—NH—, —NH—C(=O)—O—, —O—C(=O)—NH—, —NH—C(=O)—NH—, —C(=O)—C(=O)—, —O—C(=O)—C(=O)—O—, —NH—C(=O)—C(=O)—NH—, —NH—C(=O)—C(=O)—O— or —O—C(=O)—C(=O)—NH—;

Z$^1$ and Z$^2$ are independently H$_2$N—, O=C=N—, Cl—C(=O)—, Br—C(=O)—, HO—C(=O)—,

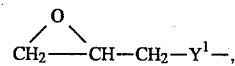

H$_2$N—C(R$^9$)(R$^{10}$)—(CH$_2$)$_w$—Y$^1$— or R$^{11}$—O—C(=O)—;

R$^9$ and R$^{10}$ are independently hydrogen or a substituted or unsubstituted alkyl radical of 1 to 4 carbons;

R$^{11}$ is an alkyl radical of 1–4 carbons, benzyl or phenyl;

t, x, y and z are independently 0 or 1;

w is an integer from 1 to 12; and substituents for any of R$^1$, R$^2$, R$^3$, R$^4$, R$^5$, R$^6$, R$^7$, R$^8$, R$^9$ or R$^{10}$ are independently one or more of chloro, bromo, fluoro, cyano, hydroxy, amino, sulfo, carboxy, nitro, alkoxy of 1 to 12 carbons, alkylamino of 1 to 12 carbons, acyloxy of 1 to 12 carbons, alkenoyloxy of 3 to 12 carbons, alkenylamino of 3 to 12 carbons, aroyloxy of 7 to 15 carbons, aroylamino of 7 to 15 carbons, phthalimido, alkoxycarbonyloxy of 2 to 13 carbons, alkoxycarbonylamino of 2 to 13 carbons, alkenyloxycarbonyloxy of 3 to 12 carbons, alkenyloxycarbonylamino of 3 to 12 carbons, aryloxycarbonyloxy of 7 to 15 carbons, alkylaminocarbonyloxy of 2 to 13 carbons, arylaminocarbonyloxy of 7 to 15 carbons, aralkylaminocarbonyloxy of 7 to 16 carbons, alkylsulfonyloxy of 1 to 8 carbons, alkylsulfonylamino of 1 to 8 carbons, arylsulfonylamino of 6 to 11 carbons or epoxyalkoxycarbonyl of 2 to 13 carbons.

2. The compound according to claim 1 wherein $R^1$, $R^2$, $R^6$ and $R^7$ are independently a substituted or unsubstituted alkyl diradical of 1 to 10 carbons, a substituted or unsubstituted cycloalkyl diradical of 5 to 12 carbons, a substituted or unsubstituted bicycloalkyl diradical of 7 to 10 carbons, a substituted or unsubstituted bicycloalkenyl diradical of 7 to 10 carbons, a substituted or unsubstituted alkenyl diradical of 2 to 8 carbons, a substituted or unsubstituted alkynyl diradical of 2 to 8 carbons, a substituted or unsubstituted aralkyl diradical of 7 to 12 carbons, a substituted or unsubstituted naphthyl diradical or a substituted or unsubstituted diradical of Formula II;

$R^3$ is a substituted or unsubstituted alkyl diradical of 1 to 12 carbons, a substituted or unsubstituted aralkyl diradical of 7 to 12 carbons, a substituted or unsubstituted naphthyl diradical or a substituted or unsubstituted diradical of Formula II;

$Z^1$ and $Z^2$ are independently —N=C=O, Cl—C(=O)—, HO—C(=O)—,

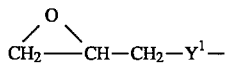

or $R^{11}$—O—C(=O)—; and substituents for any of $R^1$, $R^2$, $R^3$, $R^6$ and $R^7$ are independently one or two of chloro, bromo, amino, carboxy, alkoxy of 1 to 6 carbons, acyloxy of 2 to 5 carbons, alkenoyloxy of 3 to 5 carbons or aroyloxy of 7 to 10 carbons.

3. The compound according to claim 1 wherein $R^1$, $R^2$, $R^6$ and $R^7$ are independently a substituted or unsubstituted alkyl diradical of 1 to 6 carbons, a substituted or unsubstituted cycloalkyl diradical of 5 to 7 carbons, a substituted or unsubstituted bicycloalkyl diradical of 7 to 8 carbons, a substituted or unsubstituted bicycloalkenyl diradical of 7 to 8 carbons, a substituted or unsubstituted alkenyl diradical of 2 to 4 carbons, a substituted or unsubstituted aralkyl diradical of 7 to 12 carbons or a substituted or unsubstituted diradical of Formula II;

$R^3$ is an alkyl diradical of 1 to 8 carbons;

$R^4$ and $R^5$ are independently alkyl of 1 to 3 carbons;

$Y^1$, $Y^2$ and $Y^3$ are independently —C(=O)—O— or —O—C(=O)—;

$Z^1$ and $Z^2$ are independently —N=C=O, Cl—C(=O)— or —HO—C(=O)—; and substituents for any of $R^1$, $R^2$, $R^3$, $R^6$ and $R^7$ are independently chloro, hydroxy, carboxy, alkoxy of 1 to 4 carbons, acyloxy of 2 to 3 carbons or alkenoyloxy of 3 to 5 carbons.

* * * * *